United States Patent
Hasegawa

(10) Patent No.: US 8,269,824 B2
(45) Date of Patent: Sep. 18, 2012

(54) ELECTRONIC ENDOSCOPE SYSTEM FOR ESTIMATING AND PRODUCING SPECTRAL IMAGE OF ARBITRARY WAVELENGTH BAND FROM IMAGE SIGNALS CAPTURED UNDER GENERAL ILLUMINATION LIGHT AND THOSE CAPTURED UNDER SPECIFIC ILLUMINATION LIGHT

(75) Inventor: Kazuhide Hasegawa, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 1444 days.

(21) Appl. No.: 11/826,585

(22) Filed: Jul. 17, 2007

(65) Prior Publication Data

US 2008/0018733 A1    Jan. 24, 2008

(30) Foreign Application Priority Data

Jul. 21, 2006    (JP) .................................. 2006-199508

(51) Int. Cl.
 *A61B 1/06*    (2006.01)
(52) U.S. Cl. ................. 348/68; 348/45; 348/49; 348/51; 348/54; 348/55; 348/56; 348/57; 600/109
(58) Field of Classification Search ..................... 348/45, 348/49, 51, 54, 55, 56, 57, 68; 600/109
See application file for complete search history.

(56) References Cited

U.S. PATENT DOCUMENTS

| 5,687,730 | A | 11/1997 | Doiron et al. | |
|---|---|---|---|---|
| 2003/0176768 | A1* | 9/2003 | Gono et al. | 600/109 |
| 2004/0225222 | A1* | 11/2004 | Zeng et al. | 600/476 |
| 2009/0028407 | A1* | 1/2009 | Seibel et al. | 382/131 |

FOREIGN PATENT DOCUMENTS

| EP | 1 702 557 | A2 | 9/2006 |
|---|---|---|---|
| EP | 1 994 875 | A1 | 11/2008 |
| JP | 2002-034908 | A | 2/2002 |
| JP | 2002-095635 | A | 4/2002 |
| JP | 2002-296114 | A | 10/2002 |
| JP | 2003-061909 | A | 3/2003 |
| JP | 2003-093336 | A | 4/2003 |
| JP | 2004-202217 | A | 7/2004 |
| JP | 2005-198794 | A | 7/2005 |

(Continued)

OTHER PUBLICATIONS

EP Communication, dated Jun. 25, 2010, issued in corresponding EP Application No. 07013608.0, 7 pages.

(Continued)

*Primary Examiner* — Haresh N Patel
(74) *Attorney, Agent, or Firm* — Sughrue Mion, PLLC

(57) ABSTRACT

An illuminator of an electronic endoscope system is provided with a light emission mechanism that consists of a light source emitting white light as general illumination light and an optical chopper that turns a disc at a revolution speed in front of the light source. The disc consists of transparent glass sectors and filter sectors. Each time the general illumination light passes through the filter sectors, the illuminator emits specific illumination light having different spectral characteristics from those of the general illumination light, so a CCD outputs two kinds of image signals under the general illumination light and the specific illumination light. A spectral image producer produces a spectral image of arbitrary wavelength bands from the two kinds of image signals, whereas a general image producer produces a general image from those image signals captured under the general illumination light.

5 Claims, 5 Drawing Sheets

FOREIGN PATENT DOCUMENTS

| | | |
|---|---|---|
| JP | 2005-223700 A | 8/2005 |
| JP | 2005-260480 A | 9/2005 |
| JP | 2006-187426 A | 7/2006 |
| JP | 2007-244681 A | 9/2007 |
| WO | 95/17845 A1 | 7/1995 |
| WO | 2005/071372 A1 | 8/2005 |

OTHER PUBLICATIONS

Notification of Reasons for Refusal, dated Jul. 20, 2011, issued in corresponding JP Application No. 2006-199508, 7 pages in English and Japanese.

* cited by examiner

ELECTRONIC ENDOSCOPE SYSTEM FOR ESTIMATING AND PRODUCING SPECTRAL IMAGE OF ARBITRARY WAVELENGTH BAND FROM IMAGE SIGNALS CAPTURED UNDER GENERAL ILLUMINATION LIGHT AND THOSE CAPTURED UNDER SPECIFIC ILLUMINATION LIGHT

FIELD OF THE INVENTION

The present invention relates to an electronic endoscope system that can get a spectral image of arbitrary wavelength bands from an internal body part.

BACKGROUND OF THE INVENTION

Medical diagnoses utilizing an electronic endoscope have widely been practiced in the medical field these days. The electronic endoscope has a solid state imaging device like a CCD, which is built in an end of an elongated probing portion that is introduced into a test body, so that the CCD takes an image signal from an internal body site. The image signal is processed in a processor, to display an image of the internal body site on a monitor.

In the field of medical diagnosis utilizing the electronic endoscope, an imaging method called Narrow Band Imaging (NBI) is in the limelight, wherein light of a narrow wavelength band is projected toward a target body part to inspect, to produce an image from reflected light. The image captured this way is called a spectral image, for discrimination from a general image that is produced from white light reflected from the target body part. The NBI method makes it easy to obtain such images that facilitate finding out lesions, e.g. an image enhancing blood vessels in a sub-mucosal layer, and an image enhancing structure of an internal organ, like a stomach wall or surface tissues of intestines, without the need for spraying some pigment on the target part or injecting some contrast agent like indocyanine green (ICG).

Also a technique has recently been brought into practice, wherein a spectral image is obtained from a general image as produced from white light reflected from the target body part, by subjecting the general image to linear approximation through dimension reduction using principal component analysis, or spectral estimation such as Wiener estimation.

For the sake of improving accuracy of spectral estimation, it is effective to increase the number of spectral sensitivity bands from the three bands for red, green and blue of the solid state imaging device. This is called band-multiplication of spectral sensitivity, and a lot of methods for the band multiplication have conventionally been suggested in the field of electronic endoscope and other fields as well. In an example of the conventional methods, as disclosed in JPA 2002-296114, two kinds of band pass filters are alternatively set in front of a lens that forms an image of a subject on photographic film, to capture a pair of images of the same subject through the respective filters, and a spectral image is produced from the images of one pair.

According to another method as suggested in JPA 2005-223700, incident light is separated through a color separation prism into a plurality of light beams of different wavelength bands, and the separated light beams are captured by a corresponding number of solid state imaging devices placed at exit surfaces of the color separation prism, so that a spectral image is produced from the captured images.

JPA 2005-260480 suggests an imaging apparatus, wherein a branching optical system is disposed between an image-forming optical system for forming an image of a subject and a single-chip color imaging device, so that the branching optical system divides a luminous flux of the subject image into a plurality of light beams, and converges the divided light beams individually onto divisional image forming surfaces.

The above three prior arts need the color separation prism, the filters or the branching optical system to be disposed between the imaging lens and the imaging device. Therefore, in order to apply these prior arts to the electronic endoscope, it is necessary to dispose the color separation prism, the filters or the branching optical system beside the solid state imaging device in the tip of the probing portion of the electronic endoscope. Then, the probing portion should be broader than conventional, and it would increase the load on the patients.

SUMMARY OF THE INVENTION

In view of the foregoing, a primary object of the present invention is to provide an electronic endoscope system that improves accuracy in the spectral estimation without the need for broadening the probing portion of the electronic endoscope.

An electronic endoscope system of the present invention comprises a light emission device for emitting white light as general illumination light and specific illumination light having different spectral characteristics from those of the general illumination light; an electronic endoscope having a lighting window for projecting the illumination light from the light emission device toward a body part to inspect inside a test body, and a solid state imaging device for outputting image signals corresponding to light beams reflected from the body part to inspect; a processor for producing images from image signals outputted from the solid state imaging device, the processor comprising a device for estimating and producing a spectral image of an arbitrary wavelength band from image signals captured under the general illumination light and image signals captured under the specific illumination light; and a monitor for displaying images produced by the processor.

The specific illumination light is preferably obtained from the general illumination light through at least an optical filter having such spectral transmission characteristics that spectral sensitivity characteristics of the solid state imaging device are virtually modified under the specific illumination light from those under the general illumination light.

The spectral transmission characteristics of the filter preferably show a linear characteristic curve that inclines upward or downward to an axis of wavelength so that spectral sensitivity bands of the solid state imaging device are virtually shifted under the specific illumination light from those under the general illumination light.

According to a preferred embodiment, the light emission device comprises a light source emitting the general illumination light, and the optical filter movable into and out of an optical path of the light source.

More preferably, the light emission device comprises an optical chopper having a disc that turns at a predetermined revolution speed in the optical path of the light source, the disc having transparent portions letting the general illumination light pass through them, and filter portions made of the optical filter. The filter portions are arranged in alternation with the transparent portions at constant intervals around a circumference of the disc.

According to another preferred embodiment, the light emission device comprises first and second light sources that emit the general illumination light, the optical filter placed in front of the second light source, and a switch for turning the second light source on and off. Thus, the light emission device emits the specific illumination light while the second light source is on.

The light emission device preferably emits the general illumination light and the specific illumination light alternately at predetermined intervals. In that case, it is preferable to provide the processor with a buffer memory for storing temporarily image signals of a preceding image frame captured during the preceding emission of the general illumination light, and an image producer for producing a general image from those image signals captured under the general illumination light, wherein the image producer interpolates an image frame between the preceding image frame and a present image frame captured during the present emission of the general illumination light, on the basis of image signals of the present image frame and the image signals of the preceding image frame read out from the buffer memory.

According to the electronic endoscope system of the present invention, the spectral image of an arbitrary wavelength band is estimated and produced from the image signals captured under the general illumination light and the image signals captured under the specific illumination light. Thereby, the spectral sensitivity bands of the solid state imaging device are multiplied without the need for mounting any band-multiplying device in a tip of a probing portion of the endoscope in association with the solid state imaging device or an optical system for forming an image on the solid state imaging device. Thus, it is unnecessary to broaden the tip of the probing portion of the electronic endoscope.

BRIEF DESCRIPTION OF THE DRAWINGS

The above and other objects and advantages of the present invention will be more apparent from the following detailed description of the preferred embodiments when read in connection with the accompanied drawings, wherein like reference numerals designate like or corresponding parts throughout the several views, and wherein.

DESCRIPTION OF THE PREFERRED EMBODIMENTS

Figure 1:
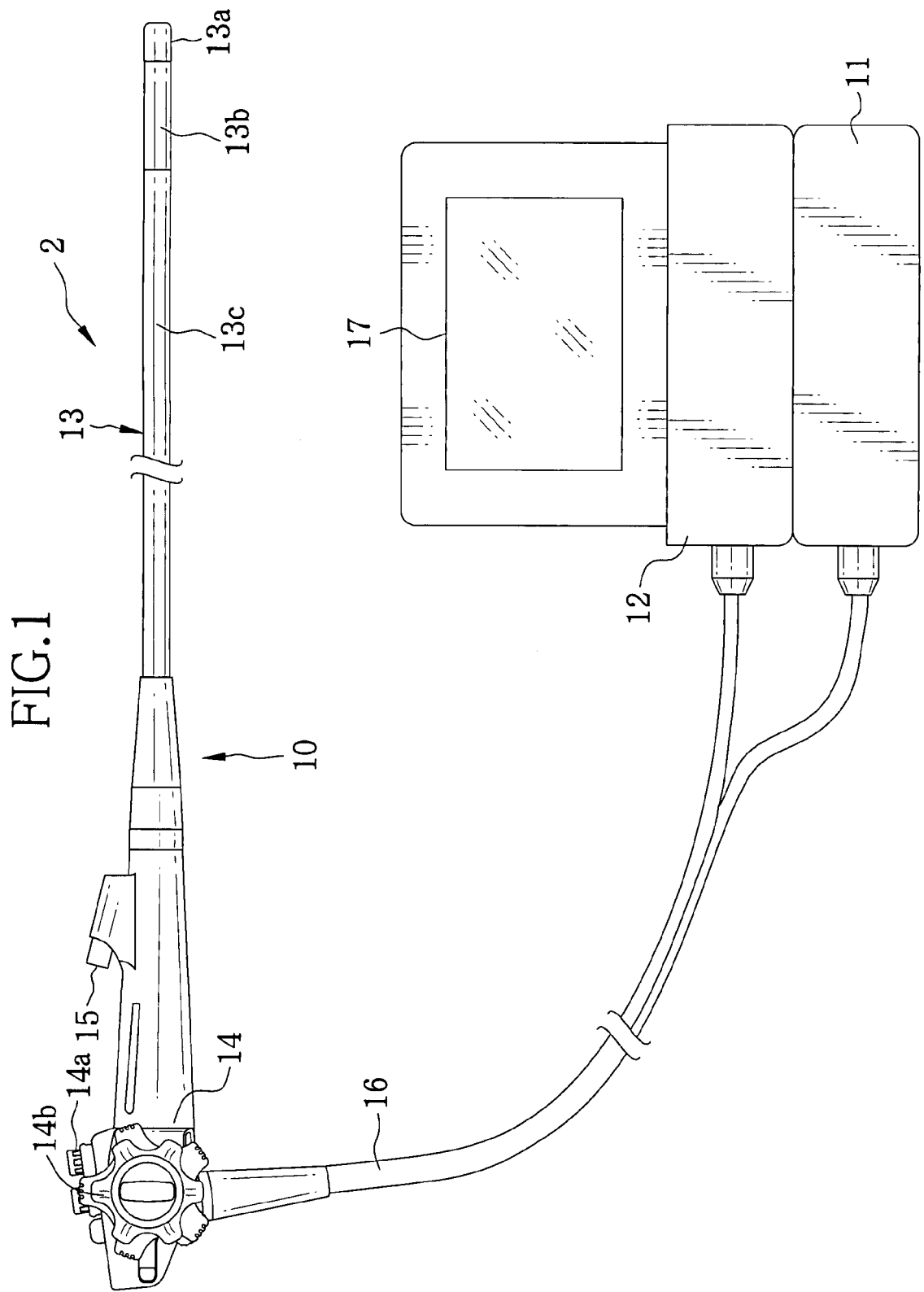
FIG. 1 is a schematic diagram illustrating an electronic endoscope system.

FIG. 1 shows an electronic endoscope system 2, which consists of an electronic endoscope 10, an illuminator 11 and a processor 12. The electronic endoscope 10 is provided with a probing portion 13 that is introduced into a test body, and a control section 14 that is joined to a base end of the probing section 13.

Figure 2:
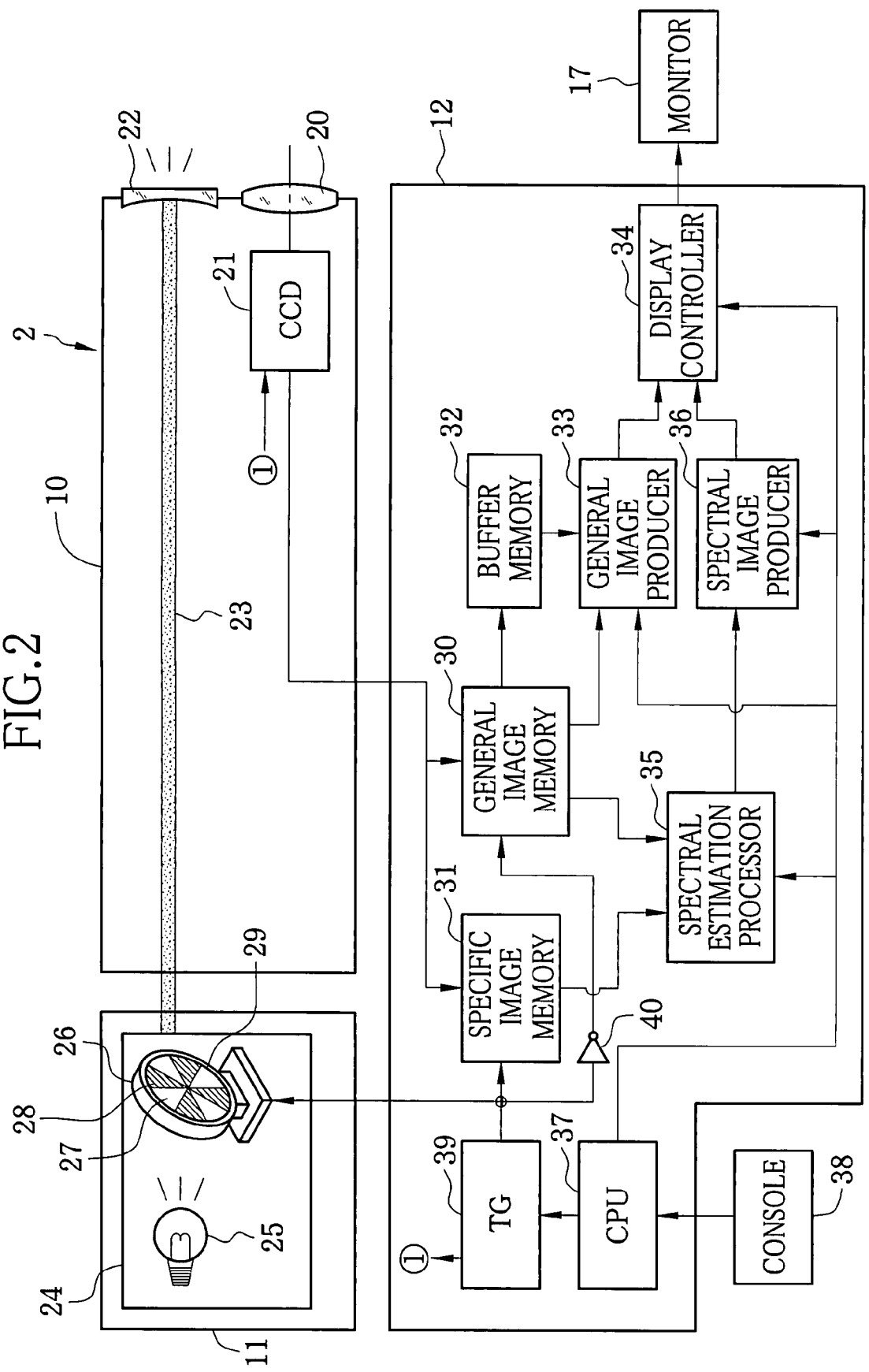
FIG. 2 is a block diagram illustrating the electronic endoscope system.

A tip portion 13a is mounted in a distal end of the probing section 13. Inside the tip portion 13a, as shown in FIG. 2, there are mounted an objective lens system 20 for forming an optical image of a target body part to inspect, a CCD 21 for capturing the optical image of the target body part, and an lighting widow 22 for projecting light from the illuminator 11 toward the target body part. The tip portion 13a is further provided with a not-shown nozzle, which ejects the water or the air in response to an operation on a watering/airing switch 14b of the control section 14, to wash or blow dirt away from the surface of an inspection window that protects the objective lens system 20. The image captured by the CCD 21 is sent to the processor 12 through a code 16, and is displayed on a monitor 17 of the processor 12.

Behind the tip portion 13a is provided a curving section 13b consisting of a number of linked curving segments. By operating an angle knob 14b on the control section 14, a number of wires, which are not shown but extend in the probing section 13, are pulled and pushed to bend the curving section 13b appropriately, thereby to direct the tip portion 13a to the target body portion inside the test body.

A flexible section 13c is provided behind the curving section 13b. The flexible section 13c has a length of several meters so that the tip portion 13a can reach the target body part while the operator grips and manipulates the control section 14 at a distance enough to prevent interference with the patient.

As shown in FIG. 2, the lighting widow 22 is joined to one end of a light guide 23, which extends through the probing portion 13, the control section 14 and the code 16, and is connected to a light emission mechanism 24 that is built in the illuminator 11.

The light emission mechanism 24 consists of a light source 25 and an optical chopper 26. An example of the light source 25 is a halogen lamp that emits white light, hereinafter called general illumination light. The optical chopper 26 has a round disc 29 that consists of transparent glass sectors 27 and filter sectors 28 as hatched in the drawing, which alternate with each other at regular intervals. That is, the sectors 27 and 28 are equal in size. As the disc 29 turns at a given revolution speed, the general illumination light from the light source 25 alternately passes through one of the glass sectors 27 and one of the filter sectors 28. As passing through the filer sector 28, illumination light of a limited wavelength band, hereinafter called specific illumination light, is obtained from the general illumination light. As a result, the general illumination light through the glass sectors 27 and the specific illumination light through the filter sectors 28 alternately enter the light guide 23. The interval of alternation between the general illumination light and the specific illumination light is determined by the alternating intervals between the glass sector 27 and the filter sector 28 as well as the revolution speed of the disc 29. In the present embodiment, the interval of alternation between the general illumination light and the specific illumination light is synchronized with the imaging interval of the CCD 21, that is, the time interval at which the CCD 21 outputs three-color (RGB) image signals of one frame.

Figure 3A:
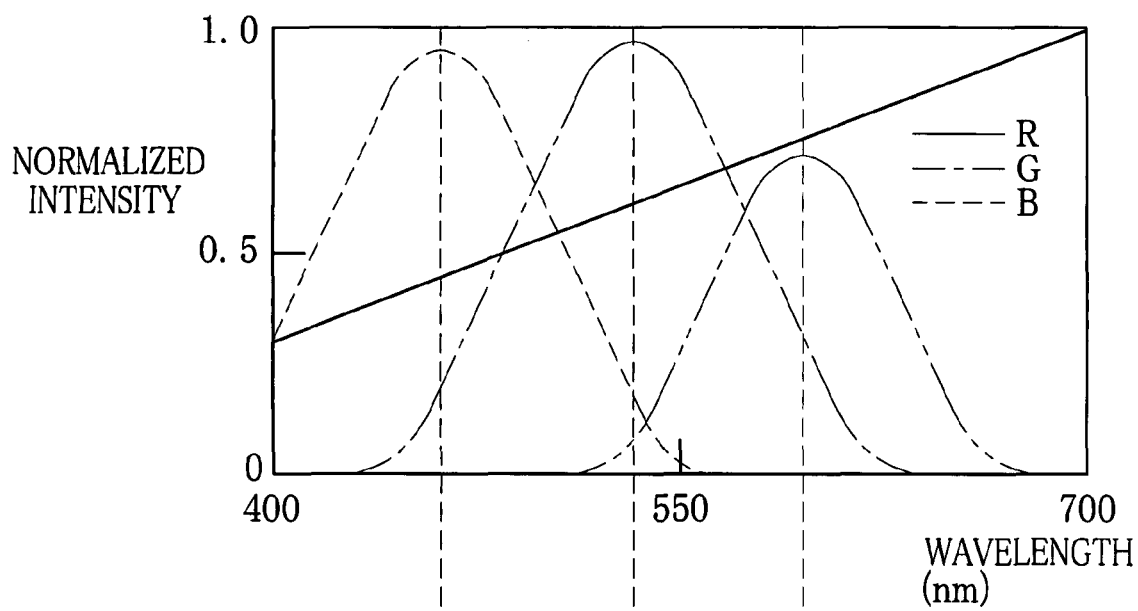
FIG. 3A is a graph illustrating actual spectral sensitivity curves of a CCD and a spectral transmittance curve of a filter.

As indicated by a solid line in FIG. 3A, the filter 28 has a linear spectral transmittance curve that inclines to the axis of the wavelength, upward toward the longer wavelength side, wherein the filter 28 has a transmittance of 30% to a light beam having a wavelength of 400 nm and a transmittance of 100% to a light beam having a wavelength of 700 nm. Because the test body to inspect with the electronic endoscope 10 is so dark that the CCD 21 carris out imaging with the illumination light from the lighting widow 22 alone, it is unnecessary to take account of influences from other illuminants. Therefore, while the specific illumination light is being projected, the CCD 21 is considered to have virtual spectral sensitivity, of which characteristic curves are obtained as products of actual spectral sensitivity curves of the CCD 21 under the general illumination light, as shown by curved lines in FIG. 3A, and the linear spectral transmittance curve of the filter 28.

Figure 3B:
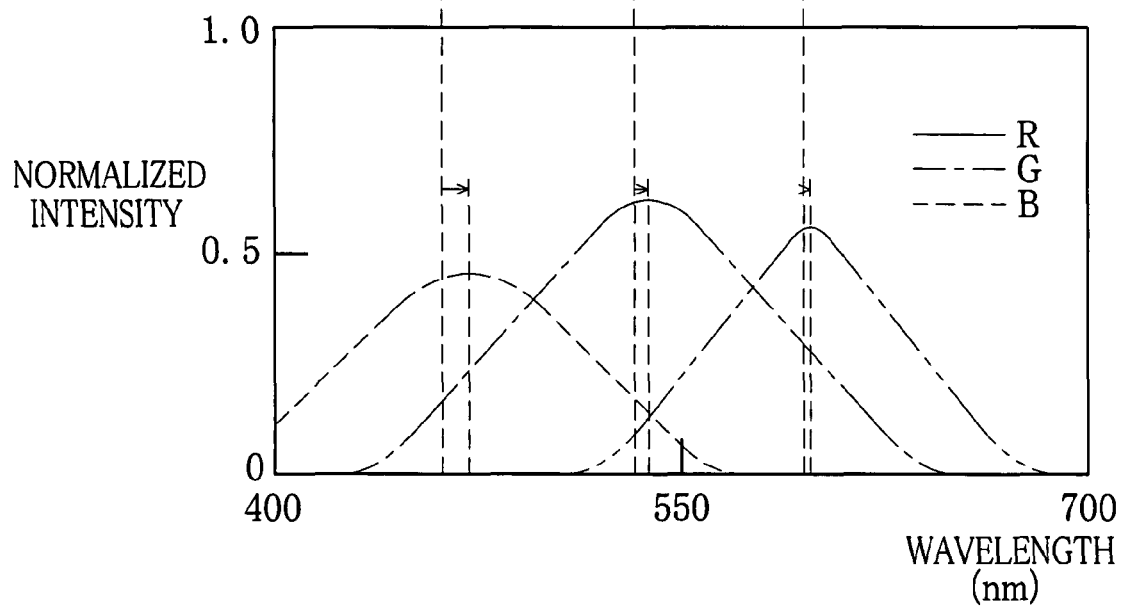
FIG. 3B is a graph illustrating virtual spectral sensitivity curves of the CCD to a specific illumination light projected through the filter.

In more detail, since the spectral transmittance curve of the filter 28 inclines upward toward the long wavelength side of the wavelength axis, the virtual spectral sensitivity curves of the CCD 21 under the specific illumination light become as shown in FIG. 3B. The intensity of blue (B) having a shorter wavelength band is most suppressed as indicated by dashed lines, and the intensity of green (G) having an intermediate wavelength band is less suppressed as indicated by chain-dotted lines, whereas the intensity of red (R) having a longer wavelength band is least suppressed as indicated by phantom lines. Furthermore, intensity peaks of the respective color spectra are shifted slightly to the longer wavelength side.

Because the test body is illuminated with the general illumination light and the specific illumination light, the CCD 21 outputs three-color (RGB) image signals representative of two kinds of image frames: one is captured at the actual spectral sensitivity characteristics of the CCD 21 as shown in FIG. 3A, i.e., under the general illumination light, so it will be called a general image frame, and the other is captured at the virtual spectral sensitivity characteristics of the CCD 21 as shown in FIG. 3B, i.e., under the specific illumination light, so it will be called a specific image frame. That is, the CCD 21 may be held to have six sensitivity bands: three bands for RGB at the actual spectral sensitivity characteristics, and three bands for RGB at the virtual spectral sensitivity characteristics of the CCD 21. Since the optical chopper 26 alternates the general illumination light with the specific illumination light at the same timing as the timing of image-capturing by the CCD 21, the CCD 21 alternately outputs the image signals of one general image frame and the image signals of one specific image frame.

Referring back to FIG. 2, the general image frame and the specific image frame are fed from the CCD 21 to a general image memory 30 and a specific image memory 31 of the processor 12 respectively. The general image memory 30 is connected to a buffer memory 32. Each time the general image frame is fed to the general image memory 30, the general image memory 30 transfers the previously-stored general image frame to the buffer memory 32. Thus, the buffer memory 32 stores the preceding general image frame that had been captured before the CCD 21 captured the specific image frame that is presently stored in the specific image memory 31.

The general image memory 30 and the buffer memory 32 are connected to a general image producer 33. The general image producer 33 reads out the general image frame from the general image memory 30, and processes the general image frame through analog signal processing such as correlated double sampling, amplification and A/D conversion, and then digital signal processing such as gradation correction, edge enhancement and gamma correction.

The general image producer 33 also reads out the preceding general image frame from the buffer memory 32. With reference to the preceding general image frame read out from the buffer memory 32 and the general image frame read out from the general image memory 30, the general image producer 33 detects motion vectors between the present and preceding general image frames. From the detection result, the general image producer 33 derives an interpolative general image frame that would be captured if the general illumination light were projected at the time when the specific image frame was captured between the present and preceding general image frames. Then, the general image producer 33 interpolates the derived general image frame between the present and preceding general image frames, and outputs the general image frames to a display controller 34 to display a general image as a motion picture. This process is called motion interpolation.

The general image memory 30 and the specific image memory 31 are connected to a spectral estimation processor 35. The spectral estimation processor 35 reads out the general image frame and the specific image frame from the respective memories 30 and 31, and serves the read image frames for linear approximation that is achieved by dimension reduction using principal component analysis, and spectral estimation such as Wiener estimation.

Concretely, through the spectral estimation, reflectance spectra of the target body part in the wavelength range of visible light beams, i.e. from 400 nm to 700 nm, are estimated from the general image signals and the specific image signals, since the general image signals reflect the actual spectral sensitivities of the CCD 21 to the three-color (RGB) bands under the general illumination light, whereas the specific image signals reflect the virtual spectral sensitivities of the CCD 21 to the three-color bands under the specific illumination light.

A spectral image producer 36 produces a spectral image of arbitrary wavelength bands from the general image signals and the specific image signals on the basis of the results of the spectral estimation in the spectral estimation processor 35, wherein the spectral image includes such a composite image that is produced by allocating three image spectra of different wavelength bands, e.g. 500 nm, 450 nm and 400 nm, to the three bands for RGB. The spectral image producer 36 outputs the produced spectral image to the display controller 34.

Figure 4:
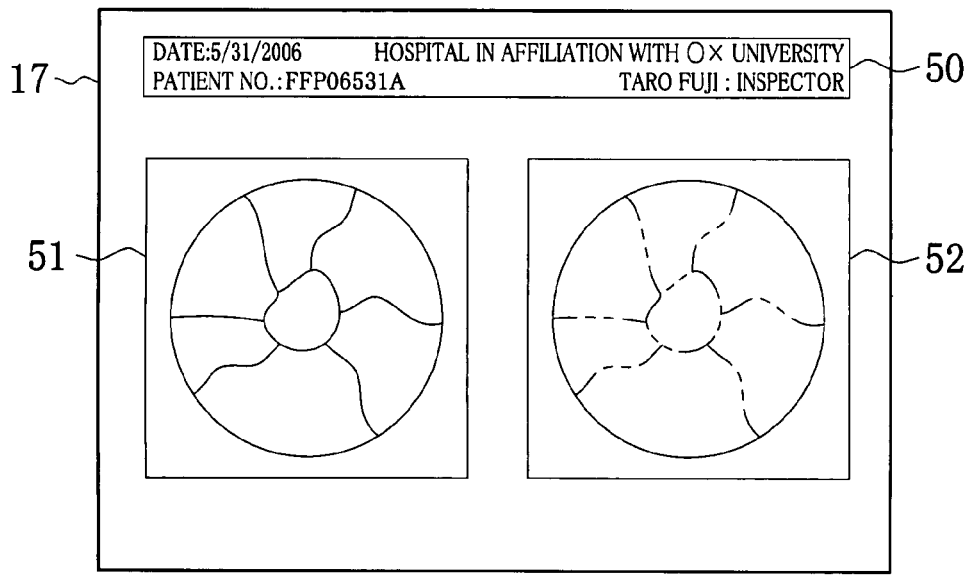
FIG. 4 is an explanatory diagram illustrating a display condition of a monitor.

As shown in FIG. 4, the display controller 34 controls the monitor 17 to display a general image 51 produced from the general image producer 33 and a spectral image 52 produced from the spectral image producer 36 side by side on a screen along with information 50 on the place and date of inspection and the patient. By operating on a control panel 38, see FIG. 2, the operator can select either the general image 51 or the spectral image 52 to display on the monitor 17.

Referring again back to FIG. 2, a CPU 37 supervises the overall operation of the processor 12. To the CPU 37 is connected the control panel 38 for the operator to set up and control the operation of the processor 12. The CPU 37 is also connected to a timing generator (TG) 39. The timing generator 39 is connected to the optical chopper 26 and the specific image memory 31, and via a NOT gate 40 to the general image memory 30.

The timing generator 39 generates a synchronizing signal under the control of the CPU 37, to drive the optical chopper 26, the general image memory 30 and the specific image memory 31 respectively at predetermined intervals. The disc 29 of the optical chopper 26 rotates at the revolution speed determined by the synchronizing signal. The specific image memory 31 picks up the specific image signals from the CCD 21 at the timing determined by the synchronizing signal. The general image memory 30 picks up the general image signals from the CCD 21 at the timing determined by an inverted synchronizing signal that is obtained by inverting the synchronizing signal through the NOT gate 40. Thus the timing of picking up the specific image signals alternates with the timing of picking up the general image signals.

To use the electronic endoscope system 2 for inspecting an internal part of a test body, the electronic endoscope 10, the illuminator 11 and the processor 12 are powered on, and the probing portion 13 is introduced into the test body, so that the CCD 21 captures images of the internal part of the test body while the internal part is being illuminated with light projected from the lighting widow 22. The images captured by the CCD 21 are displayed on the monitor 17.

As the disc 29 of the optical chopper 26 turns at the revolution speed determined by the synchronizing signal from the timing generator 39, the illuminator 11 projects the general illumination light and the specific illumination light alternating at the same intervals as the imaging intervals of the CCD 21. The illumination light is conducted through the light guide 23 to the lighting widow 22, and is projected from the lighting widow 22 toward the target body part to inspect.

Then, an optical image of the target body part is formed through the objective lens system 20 on an imaging surface of the CCD 21, so the CCD 21 outputs three-color image signals corresponding to the optical image. Since the target body part is illuminated alternately with the general illumination light and the specific illumination light in synchronism with the imaging interval per frame of the CCD 21, the CCD 21 outputs the general image frame and the specific image frame alternately.

The general image frame outputted from the CCD 21 is picked up by the general image memory 30 at the timing determined by the inverted synchronizing signal from the NOT gate 40. The general image signal picked up by the general image memory 30 is sequentially read by the general image producer 33 and the spectral estimation processor 35. Each time the general image frame is fed from the CCD 21 to the general image memory 30, the general image memory 30 transfers the previously stored preceding general image frame to the buffer memory 32.

The general image producer 33 subjects the general image frame as read out from the general image memory 30 to the analog and digital signal processing. The general image producer 33 also reads out the preceding general image frame from the buffer memory 32, and executes the motion interpolation process to drive a general image frame from the present general image frame read out from the general image memory 30 and the preceding general image frame read out from the buffer memory 32, and interpolate the derived image frame between the present and preceding general image frames. The general image producer 33 outputs the produced general image to the display controller 34.

On the other hand, the specific image frame outputted from the CCD 21 is picked up by the specific image memory 31 at the timing determined by the synchronizing signal from the timing generator 39. The spectral estimation processor 35 sequentially reads the specific image frame from the specific image memory 31 and the general image frame from the general image memory 30. The spectral estimation processor 35 executes the spectral estimation process using the present general image frame read out from the general image memory 30 and the preceding general image frame read out from the buffer memory 32. On the basis of the results of the spectral estimation, the spectral image producer 36 produces the spectral image from the general image frame and the specific image frame, and outputs the spectral image to the display controller 34. The display controller 34 drives the monitor 17 to display the general image and the spectral image simultaneously or individually.

As described so far, the illuminator 11 of the electronic endoscope system 2 has the light emission mechanism 24 for projecting the general illumination light and the specific illumination light alternately, so that the spectral estimation processor 35 executes the spectral estimation process using the general image frames captured under the general illumination light and the specific image frames captured under the specific illumination light. According to this configuration, the spectral sensitivity bands of the CCD 21 are virtually multiplied without the need for disposing a band-multiplication device in the tip portion 13*a* of the probing portion 13.

Since some conventional electronic endoscope systems are provided with an optical chopper in their illuminator, these endoscope systems may be modified to have the same configurations as the above-described endoscope system 2 just by replacing a disc of the already provided optical chopper with the disc 29 and restructuring a processor of the conventional system.

According to the above embodiment, the preceding general image frame, which had been captured before the last specific image frame was captured, is stored in the buffer memory 32, so that the general image producer 33 executes the motion interpolation on the basis of the preceding general image frame and the present general image frame that is stored in the general image memory 30, to derive an general image frame to interpolate between the preceding and present general image frame. Therefore, the general image is displayed at the same frame rate as at the output of the CCD 21.

As the general image and the spectral image are displayed either side by side or one by one on the monitor 17, the inspector can promptly make an accurate medical diagnosis.

Figure 5A:
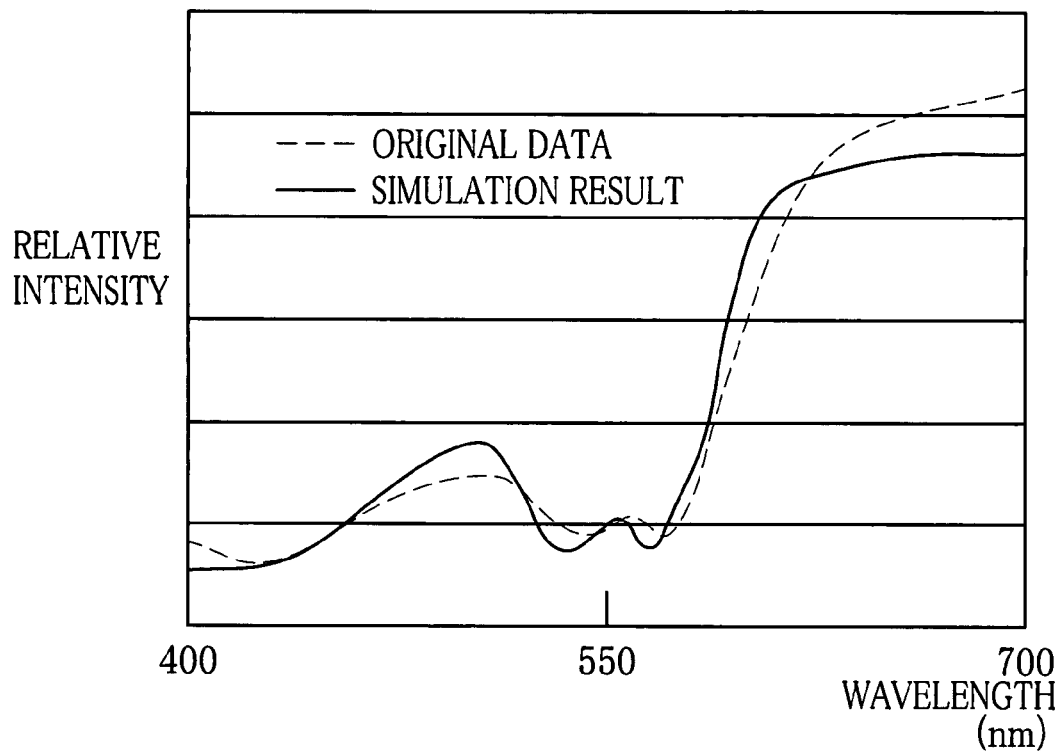
FIG. 5A is a graph illustrating a simulation result of a spectral estimation using a general image alone.
Figure 5B:
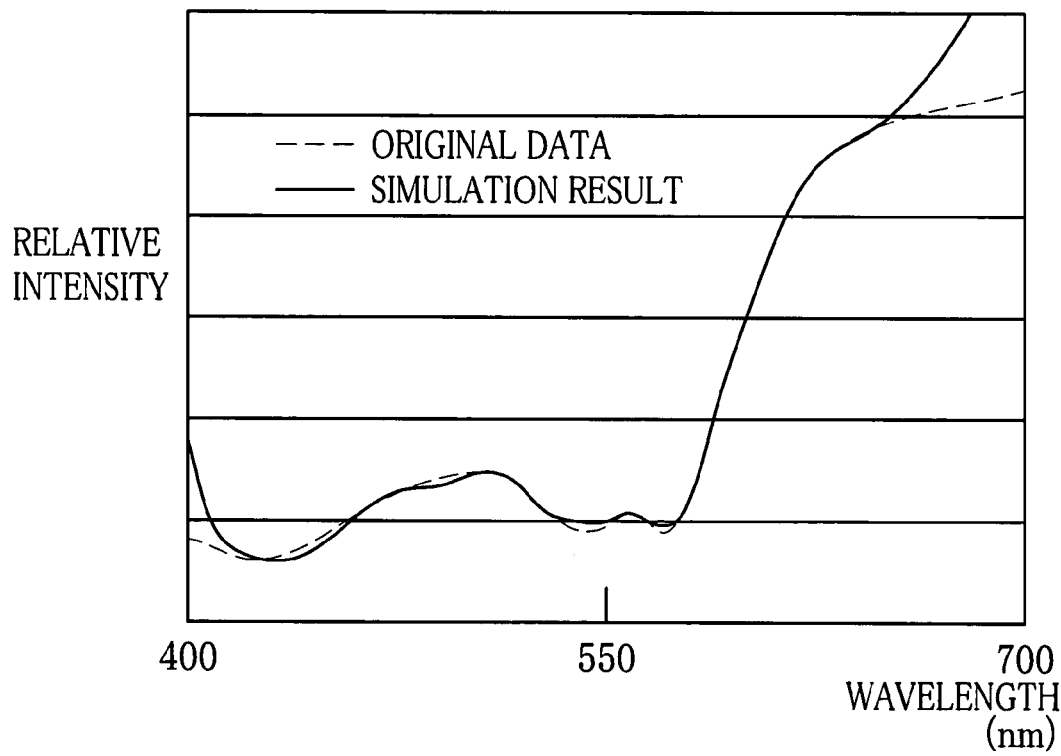
FIG. 5B is a graph illustrating a simulation result of a spectral estimation using both the general image and a specific image captured under the specific illumination light.

FIGS. 5A and 5B show a simulation result of a spectral estimation process using general image frames as conventional, and a simulation result of a spectral estimation process using general image frames and specific image frames in the way as described above. As shown in FIG. 5A, the simulation result of the conventional spectral estimation process, indicated by a solid line, does not follow well original data indicated by dashed lines in the whole range. On the other hand, as shown in FIG. 5B, the simulation result of the spectral estimation using the general and specific image frames approximately reproduces the original data in an intermediate wavelength band. From these results, it is confirmed that the accuracy of spectral estimation is improved when the general image frames and the specific image frames are used for the estimation.

Although the electronic endoscope system 2 of the above-described embodiment has the illuminator 11 whose light emission mechanism 24 uses the optical chopper 26, it is possible to use another mechanism for periodically alternating the glass 27 with the filter 28.

Figure 6:
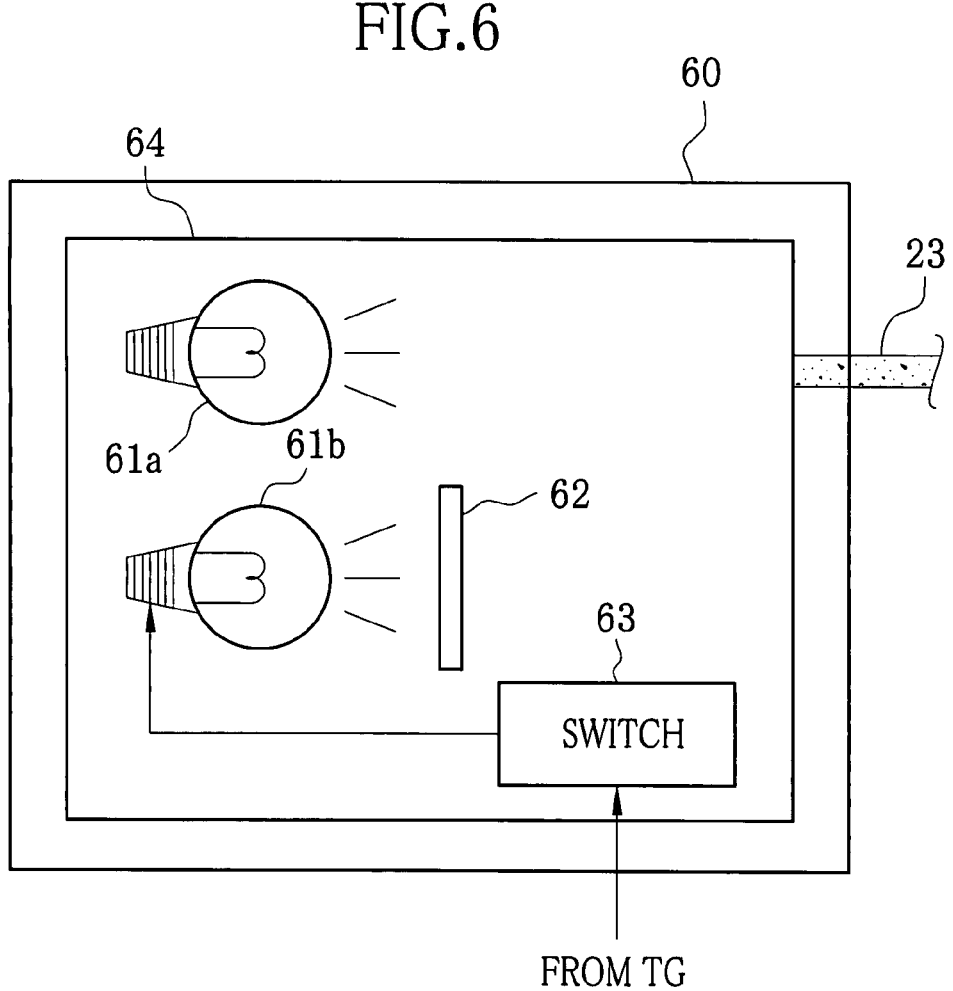
FIG. 6 is a block diagram illustrating another embodiment of an illuminator of the electronic endoscope system.

The electronic endoscope system of the present invention can use another illuminator. For example, as shown in FIG. 6, an illuminator 60 may be provided with a light emission mechanism 64 consisting of first and second light sources 61*a* and 61*b*, both of which emit the general illumination light, a filter 62 placed in front of the second light source 61*b* and a switch 63 connected to the second light source 61*b*. The filter 62 has the same spectral transmittance curve as the filter 28. The switch 63 turns the second light source 61*b* on and off in response to the synchronizing signal from the timing generator 39.

As the switch 63 turns the second light source 61*b* on and off, the light emission mechanism 64 emits the general illumination light from the first light source 61*a* while the second light source 61*b* is off, and a composite illumination light composed of the general illumination light from the first light source 61*a* and the special illumination light obtained through the filter 62 while the second light source 61*b* is on. The interval of alternation between the general illumination light and the composite illumination light is determined by the synchronizing signal from the timing generator 39. Thus, the general illumination light and the composite illumination light are alternately projected through the light guide 23.

It is also possible to drive the first light source 61a alternately with the second light source 61b.

Instead of the second light source 61b and the filter 62, it is possible to use a light source that directly emits the special illumination light, i.e. the light having the same spectral characteristics as shown in FIG. 3B.

Although the filters 28 and 62 has the linear spectral transmittance curve that inclines to the wavelength axis upward toward the longer wavelength side in the above embodiment, the present invention is not to be limited to this, but another filer is usable insofar as it provides such a specific illumination light under which the spectral sensitivity characteristics of the CCD 21 are virtually modified. For example, a filter having a linear spectral transmittance curve that inclines downward toward the longer wavelength side of the wavelength axis, or a filter having a zigzag spectral transmittance curve is usable. Furthermore, although the above embodiment uses the specific illumination light of a single kind, it is possible to construct the illuminator to project two or more kinds of specific illumination light.

It is not always necessary to separate the illuminator from the electronic endoscope, but the illuminator may be built in the control section of the endoscope.

Although the present invention has been described with reference to the electronic endoscope system, the present invention is applicable to an ultrasonic endoscope system wherein an ultrasonic transducer is integrated with a CCD in a tip of a probing portion of an endoscope, so that the ultrasonic transducer projects an ultrasonic wave toward an internal body part to inspect and receives an echo signal that is reflected from the internal body part.

Thus, the present invention is not to be limited to the above embodiments but, on the contrary, various modifications will be possible without departing from the scope of claims appended hereto.

What is claimed is:

1. An electronic endoscope system comprising:
    a light emission device for emitting white light as general illumination light and specific illumination light having different spectral characteristics from those of the general illumination light;
    an electronic endoscope having a lighting window for projecting illumination light from said light emission device toward a body part to inspect inside a test body, and a solid state imaging device for outputting image signals corresponding to light beams reflected from the body part to inspect;
    a processor for producing images from image signals outputted from said solid state imaging device, said processor comprising a device for estimating and producing a spectral image of an arbitrary wavelength band from image signals captured under the general illumination light and image signals captured under the specific illumination light; and
    a monitor for displaying images produced by said processor;
    said light emission device comprising at least a light source emitting the general illumination light, and at least an optical filter for obtaining the specific illumination light from the general illumination light through said optical filter, said optical filter having spectral transmission characteristics, spectral sensitivity characteristics of said solid state imaging device being virtually modified under the specific illumination light from those under the general illumination light;
    the spectral transmission characteristics of said optical filter show a linear characteristic curve which inclines upward or downward to an axis of wavelength, spectral sensitivity bands of said solid state imaging device being virtually shifted under the specific illumination light from those under the general illumination light;
    said processor further comprises an image producer for producing a general image from those image signals captured under the general illumination light, and a display controller for displaying the general image and the spectral image simultaneously individually on said monitor.

2. An electronic endoscope system as recited in claim 1, wherein said optical filter is mounted movable into and out of an optical path of said light source.

3. An electronic endoscope system as recited in claim 2, wherein said light emission device comprises an optical chopper having a disc which turns at a predetermined revolution speed in the optical path of said light source, said disc having transparent portions letting the general illumination light pass through them, and filter portions made of said optical filter, said filter portions being arranged in alternation with said transparent portions at constant intervals around a circumference of said disc.

4. An electronic endoscope system as recited in claim 1, wherein said light emission device comprises first and second light sources which emit the general illumination light, said optical filter placed in front of the second light source, and a switch for turning said second light source on and off.

5. An electronic endoscope system as recited in claim 1, wherein said light emission device emits the general illumination light and the specific illumination light alternately at predetermined intervals, and said processor further comprises a buffer memory for storing temporarily image signals of a preceding image frame captured during a preceding emission of the general illumination light, and an image producer for producing a general image from image signals captured under the general illumination light, wherein said image producer interpolates an image frame between the preceding image frame and a present image frame captured during the present emission of the general illumination light on the basis of image signals of the present image frame and the image signals of the preceding image frame read out from said buffer memory.

* * * * *